United States Patent [19]
Uchino et al.

[11] Patent Number: 5,614,554
[45] Date of Patent: Mar. 25, 1997

[54] REVERSE TRANSCRIPTASE INHIBITORS AND ANTIVIRAL AGENTS

[75] Inventors: Keijiro Uchino, Atsugi; Takashi Mizuno; Sachie Murakami, both of Sagamihara; Hideki Nakashima, Yamanashi-ken; Naoki Yamamoto; Hiroshi Ogawara, both of Tokyo, all of Japan

[73] Assignee: Nippon Flour Mills Co., Ltd., Tokyo, Japan

[21] Appl. No.: 467,158

[22] Filed: Jun. 6, 1995

Related U.S. Application Data

[63] Continuation of Ser. No. 159,581, Dec. 1, 1993, abandoned.

[30] Foreign Application Priority Data

| Dec. 1, 1992 | [JP] | Japan | 4-321883 |
| Feb. 19, 1993 | [JP] | Japan | 5-030798 |
| Oct. 13, 1993 | [JP] | Japan | 5-255635 |

[51] Int. Cl.$^6$ .................... A61K 31/255; A61K 31/185
[52] U.S. Cl. .................. 514/517; 514/555; 514/576
[58] Field of Search .................. 514/517, 555, 514/576; 558/37; 562/37, 40

[56] References Cited

FOREIGN PATENT DOCUMENTS

WO90/08540  8/1990  WIPO.

OTHER PUBLICATIONS

Yoshikawa et al., CA: 85–160,525h ((1976) (Abstract of Japan Kokai 76 22,817) (1976).
Yoshikawa et al. CA: 80–6,962p (1974).
Patent Abstracts of Japan, vol. 14, No. 453(C–764)[43961], Sep. 28, 1990, JP-A-2-178232, Jul. 11, 1990.
Journal of the American Chemical Society, vol. 68, pp. 1024–1031, Jun. 1990, H.C. Reitz, et al., "Action of Sulfating Agents on Proteins and Model Substances. I. Concentrated Sulfuric Acid.".
Liu, Ming–Cheh et al, "Tyramine–O–Sulfate, In Addition to Tyrosine–O–Sulfate, is Produced and Secreted by HepG2 Human Hepatoma Cells, But Not by 3Y1 Rat Embryo Fibroblasts," Biochem. Int., vol. 21, No. 5, pp. 815–821 (1990).
Saida, T. et al, "Formation of Tyrosine O–Sulfate by Mitochondria and Chloroplasts of Euglena," Arch. Biochem. Biophys., vol. 272, pp. 237–244 (1989).
W. P. Huttner, "Determination and Occurrence of Tyrosine O–Sulfate in Proteins," Methods in Enzymology, vol. 107, pp. 200–223 (1984).
F. R. Bettelheim, "Communications to the Editor," J. Am. Chem. Soc., vol. 76, p. 2838 (1954).
L. Moroder et al, "Lynthese von Tyrosin–O–sulfat–haltigen Peptiden", Hoppe–Seyler's Z. Physiol. Chem, vol. 360, p. 787 (1979).
H.C. Reitz, et al, "Action of Sulfating Agents on Proteins and Model Substances," J. Am. Chem. Soc., vol. 68, p. 1024 (1946).

*Primary Examiner*—Nicky Chan
*Attorney, Agent, or Firm*—Oblon, Spivak, McClelland, Maier & Neustadt, P.C.

[57] ABSTRACT

The present invention provides a reverse transcriptase inhibitor and an antiviral agent comprising at least one member selected from the group consisting of sulfated tyrosines and physiologically acceptable salts thereof as an effective component; and exhibiting less toxicity and a remarkable inhibitory effect against a reverse transcriptase existing in viruses as well as a remarkable anti-AIDS viral activity.

4 Claims, 5 Drawing Sheets

Purified Sodium L-Tyrosine Sulfate

REVERSE TRANSCRIPTASE INHIBITORS AND ANTIVIRAL AGENTS

This application is a Continuation of application Ser. No. 08/159,581, filed on Dec. 1, 1993, now abandoned.

BACKGROUND OF THE INVENTION

1. Field of the Invention

The present invention relates to a reverse transcriptase inhibitor and an antiviral agent, and more specifically the present invention relates to a reverse transcriptase inhibitor and an antiviral agent which comprises sulfated tyrosines and/or physiologically acceptable salts thereof as an effective component.

2. Description of the Prior Art

AZT (azidothymidine: a reverse transcriptase inhibitor), which is the first agent for the treatment of AIDS (Aquired Immune Deficiency Syndrome), has been found to significantly delay onset and progress of AIDS. However, AZT has some problems such as a chronic toxicity caused by a long-term administration thereof and an appearance of a drug tolerance mutant of AIDS viruses. Although a therapy using AZT in combination with DDI (dideoxyinosine) was recently approved, there have been also reported grave side-effects, such as an acute pancreatitis. Both AZT and DDI are mononucleotides and affect not only a reverse transcriptase but also a human polymerase, and it follows that they lack selectivity.

A Japanese Unexamined Patent Publication (J.P. KOKAI) No. Hei 2-178232 discloses a pharmaceutical composition comprising a poly (amino acid) sulfonate as an effective component for the treatment and prevention of retrovirus infections, in particular AIDS. However the effective component is a polymeric compound having a molecular weight of from about 500 to about 500,000 dalton and therefore such compound can not be handled easily and the structure thereof, for example, a degree of sulfonation in the molecule is not specified.

There are now some antiviral agents under investigation, such as a protease inhibitor, a transcription and translation inhibitor, an uncoating inhibitor and an inhibitor against glycoration of an envelope protein of HIV.

SUMMARY OF THE INVENTION

Accordingly, an object of the present invention is to provide a novel reverse transcriptase inhibitor and a novel antiviral agent comprising a low molecular weight effective component whose structure is distinct, which component overcomes the above-mentioned disadvantages and has less toxicity.

The inventors of the present invention made an effort to search for compounds having an inhibitory activity against a reverse transcriptase of viruses in order to accomplish the above-mentioned object and then they have found that sulfated tyrosine has an excellent inhibitory activity against a reverse transcriptase and finally have completed the present invention.

According to the present invention, there is provided a reverse transcriptase inhibitor comprising at least one member selected from the group consisiting of sulfated tyrosines and physiologically acceptable salts thereof as an effective component.

Among viruses, there are, for example, retroviruses which use a reverse transcriptase to synthesize DNA from RNA templates. Therefore DNA synthesis of such viruses can be inhibited by inhibiting an activity of the reverse transcriptase.

Accordingly, the present invention also provides an antiviral agent comprising at least one member selected from the group consisting of sulfated tyrosines and physiologically acceptable salts thereof as an effective component.

Further the present invention provides an antiviral composition comprising at leaset one member selected from the group consisting of sulfated tyrosines and physiologically acceptable salts thereof as an effective component and a pharmaceutically acceptable carrier.

Preferred examples of viruses against which the antiviral agent and the antiviral composition of the present invention are effective include AIDS viruses.

DETAILED DESCRIPTION OF THE INVENTION

Figure 1:
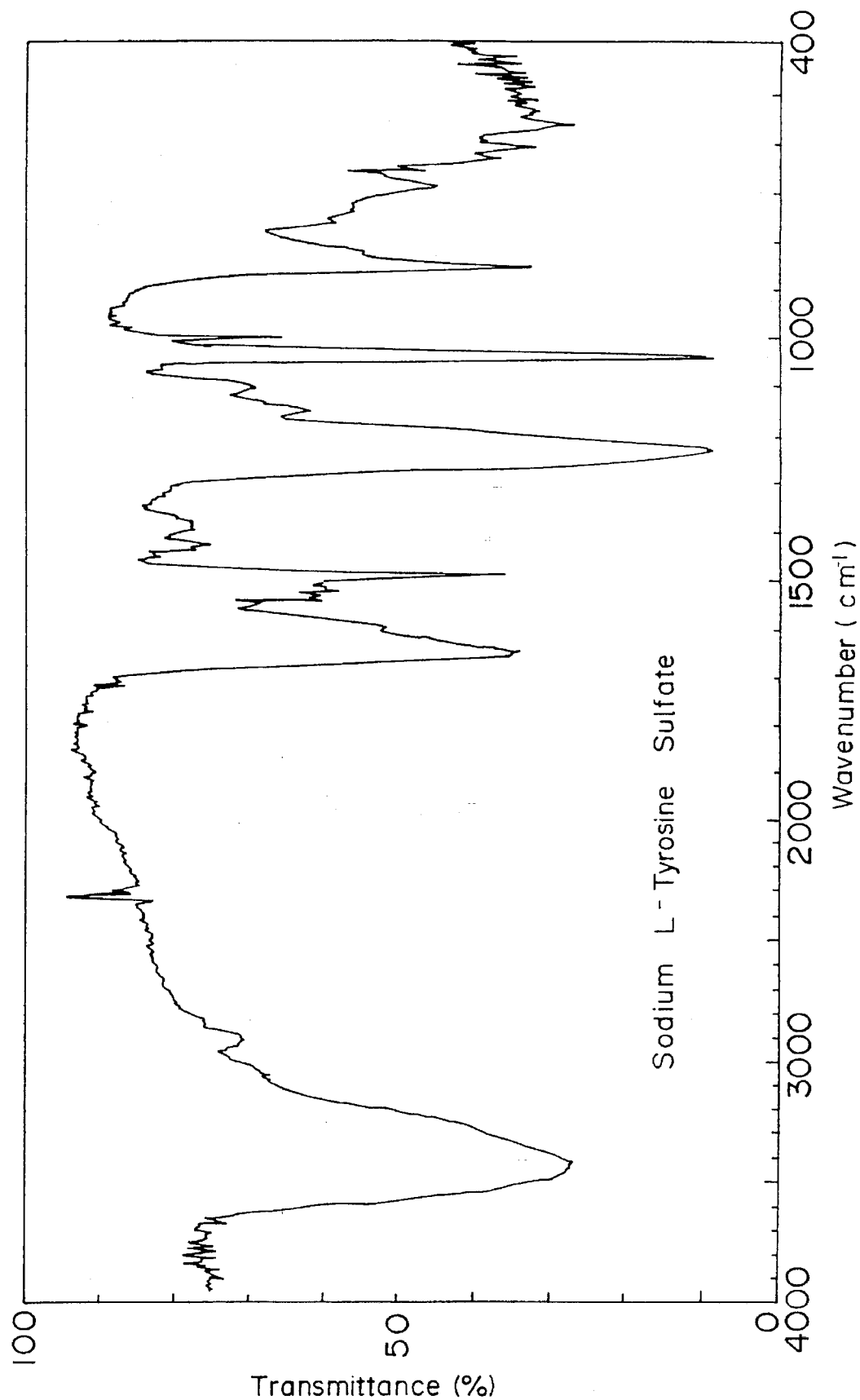
FIG. 1 is a chart of Infrared (IR) absorption spectrum of sodium L-tyrosine sulfate synthesized in Synthesis Example 1.

According to the present invention, sulfated tyrosine may be any of D-, L-isomers and DL-mixture thereof. Physiologically acceptable salts of the sulfated tyrosine include conventional metal salts, inorganic acid salts and organic acid salts, such as sodium salt, potassium salt, lithium salt, calcium salt, magnesium salt, barium salt, tetrabutylammonium salt, hydrochloride, sulfate and acetate.

The sulfated tyrosine used in the present invention as an effective component is the compound wherein at least one of the phenolic hydroxyl group and the amino group of tyrosine is sulfated. It is specifically represented by the following formula (I):

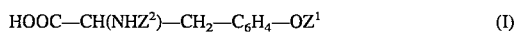

$$\text{HOOC—CH(NHZ}^2\text{)—CH}_2\text{—C}_6\text{H}_4\text{—OZ}^1 \qquad (I)$$

wherein either one of $Z^1$ and $Z^2$ is $-SO_3H$ and the other is $-SO_3H$ or hydrogen atom.

According to the present invention, particularly preferred is the sulfated tyrosine represented by the formula (I) wherein both $Z^1$ and $Z^2$ are $-SO_3H$ and physiologically acceptable salts thereof.

There has been reported a synthesis of sulfated tyrosine wherein the phenolic hydroxyl group is sulfated (which corresponds to formula (I) wherein $Z^1$ is $-SO_3H$ and $Z^2$ is hydrogen atom) by H. C. Reitz, et al. in J. Am. Chem. Soc., Vol. 68, p.1024 (1946). The sulfated tyrosine was found to be a component of proteins in 1954 (F. R. Bettelheim. J. Am. Chem. Soc. Vol. 76, p.2838 (1954)), and it has been also known that the sulfated tyrosine exists in free form in urine of mammalian (R. A. John, et al., Biochem. J. Vol. 94, p.37 (1965)). Thus it has been known that in vivo such as in animals, plants and microorganisms, sulfations of tyrosine and tyrosine residues which are present in peptides and proteins are generally conducted for detoxifications and expressions of some physiological actions, and that the sulfated tyrosine as well as the peptide and the protein comprising the sulfated tyrosine are present in vivo as a component of organisms (Review; W. P. Huttner, Methods in Enzymology (F. Wold and K. Moldave, eds.) Vol. 107, p.200–223 (1984)). Afterward, there have been reported various studies, however it has not been known that the sulfated tyrosine has an antiviral activity.

The sulfated tyrosine wherein only the phenolic hydroxyl group is sulfated has a molecular weight of 261 and the sulfated tyrosine wherein both the phenolic hydroxyl group and the amino group are sulfated has a molecular weight of 341. The molecular weights of such sulfated tyrosines are lower than that of the well-known poly(amino acid)sulfonate. Accordingly, the antigenicity which resides in the sulfated tyrosine is almost negligible and the sulfated tyrosine is advantageously capable of reducing a possible shock during the administration thereof by injections. The finding by the inventors is thoroughly unexpected because it has been conventionally supposed that no effective antiviral activity resides in the compounds which are obtained by sulfating low molecular weight compounds. A high molecular weight sulfated compound is indefinite in the position at which the sulfonic group is bound to, while the sulfated tyrosine is more definite since tyrosine possesses one hydroxyl group and one amino group in a molecule thereof.

The sulfated tyrosine used in the present invention may be prepared by treating tyrosine either in an enzymatic process or in a chemical process. As examples of such enzymatic process, (1) Saidha, T, Arch. Biochem. Biophys,. 272, 237–244 (1989); and (2) Llu, M-C, Biochem. Int., 21,815–821 (1990) are well known.

Chemical processes for preparing the sulfated tyrosine include a process comprising hydrolyzing a protein which contains sulfated tyrosine residues and a process comprising a step of sulfating tyrosine. In the latter case, any well-known sulfonating agents can be used and suitable sulfonating agents include sulfuric acid, chlorosulfonic acid, sulfur trioxide and trimethylsilyl sulfonic acid chloride and the like. An example of such processes is detailed in the report by Reitz et al. (H. C. Reitz et al., J. Am. Chem. Soc., Vol. 68, p.1024 (1946)).

Well-known salts of the sulfated tyrosine are potassium salt (F. R. Jevons, Biochem. J. 89, 621 (1963)), barium salt (L. Moroder, Hoppe-Seyler's Z. Physiol. Chem., 360, 787 (1979)) and sodium salt (W. B. Huttner, Method in Enzymology (F. Wold and K. Moldave, eds.) Vol. 107, p.200–223 (1984)).

As an example of a process for preparing the sulfated tyrosine which can be used in the present invention, a process for sulfating tyrosine will now be explained in detail.

D-isomer, L-isomer or DL-mixture of tyrosine is used as a starting compound, and the starting compound is dried, preferably on phosphorus pentoxide at 50° C. under vacuum for one night.

Solvents such as pyridine and DMF (dimethylformamide) can preferably be used, and particularly preferred is pyridine. It is desirable to use such solvent after distilled in the presence of a dehydrating agent. For example, sodium hydroxide is suitable as a dehydrating agent for pyridine.

The amount of the solvent used in the reaction may be any amount which is capable of suspending tyrosine uniformly, and it can be from one to 1,000-fold, and nomally from two to 100-fold of the weight of tyrosine which is used.

As a sulfonating agent, any well-known sulfonating agents can be used, and specific examples thereof include sulfuric acid, chlorosulfonic acid, sulfur trioxide, trimethylsilyl sulfonic acid chloride and the like. The sulfur trioxide may be used in the form of trimethylamine complex, pyridine complex or N,N-dimethylformamide complex thereof. The amount of the sulfonating agent added to tyrosine is, for example, from one to 10 equivalent, nomally from 2 to 4 equivalent and preferably 3.3 equivalent with respect to the amount of tyrosine which is used in the reaction. It is desirable to add the sulfonating agent under cooling.

The mixture of the above-mentioned tyrosine, reaction solvent and sulfonating agent is subjected to a reaction, preferably under an inert atmosphere. Inert gases which can be used are nitrogen, argon and the like.

A reaction may preferably be conducted at a temperature of from 0° to 100° C. for from one to 100 hours. At higher reaction temperature, the reaction can run more rapidly and therefore a reaction time can be suitably selected depending on a reaction temperature, and generally when a reaction time is longer, an yield of the product is higher. A reaction temperature and a reaction time can be also varied depending on a reaction solvent and a sulfonating agent which are employed in the reaction.

When trimethylamine complex of sulfur trioxide and pyridine are employed, sulfated tyrosine can be obtained by a reaction, for example, at 55° C. for 93 hours or at 90° C. for several hours. When chlorosulfonic acid and pyridine are employed, sulfated tyrosine can be obtained by a reaction, for example, at 55 for 93 hours.

It is desirable to use a reactor equipped with a drying tower so as to prevent a moisture during the reaction and there is preferably used as a desiccant, calcium chloride, sodium sulfate, magnesium sulfate, sodium hydroxide, potassium hydroxide or the like.

The reverse transcriptase inhibitor and the antiviral agent of the present invention comprise at least one compound selected from the group consisting of the above-mentioned sulfated tyrosines and physiologically acceptable salts thereof as an effective component.

The reverse transcriptase inhibitor of the present invention may further comprise any suitable additives which can be selected depending on the application thereof, provided that such additives are not detrimental to the effective components. The reverse transcriptase inhibitor of the present invention can be utilized for reagents such as an antiviral agent.

The antiviral composition of the present invention comprises at least one compound selected from the group consisting of the above-mentioned sulfated tyrosines and physiologically acceptable salts thereof as an effective component and a pharmaceutical acceptable carrier.

[Method for Administration]

The antiviral composition of the present invention may be orally and parenterally administered in the form of soft and hard capsules, tablets, granules, subtilised granules, powder for oral administration and in the form of injections, agents for instillation and other dosage forms such as suppositories which make it possible to maintain sustained absorption through mucous membrane in the form of a solid or suspended viscous liquid, for parenteral administration. When the antiviral composition of the present invention is administered in the form of injection, any of intracutaneous, subcutaneous, intramuscular, intraperitoneal and intravenous injections can be used. The antiviral composition of the present invention may further be used in external administration methods such as administration in local tissues, local painting, nebulization therapy, application as a suppository and vesicoclysis.

[Dose]

Dose of the antiviral composition of the present invention may vary depending on various factors such as methods of administration; degree of malignancy of diseases; age, conditions of diseases and general conditions of patients; and degree of progress of diseases, but in general, the dose per day of the antiviral composition ranges nomally from 1 mg to 10 g for adults expressed in the amount of the effective component.

[Method for Manufacturing Pharmaceutical Compositions]

In the antiviral composition of the present invention, the amount of the effective component to be incorporated therein may widely vary depending on a specific dosage form, but in general the amount of the effective component to be incorporated into the composition desirably ranges from about 0.3 to 15.0% by weight for oral administration or for administration by absorption through mucous membrane and from about 0.01 to 10% by weight for parenteral administration.

The effective component of the present invention may be diluted with a pharmaceutically acceptable carrier to form a pharmaceutical composition in the form of aqueous solutions, oily preparations, creams, capsules, powder, tablets, granules or the like for use in oral or parenteral administration.

In addition, for the purpose of imparting stability and acid resistance to the effective component to hence make the component withstand long term storage and to satisfactorily maintain its efficacy, the foregoing pharmaceutical compositions may be coated with pharmaceutically acceptable films to thus obtain pharmaceutical compositions exhibiting excellent stability.

Any pharmaceutical acceptable carriers such as surfactants, excipients, lubricants, auxiliary agents and pharmaceutically acceptable film-forming substances can be used in manufacturing the antiviral composition of the present invention.

The surfactants are used for improving disintegration and elution properties of the antiviral composition and specific examples thereof are alcohols, esters, polyethylene glycol derivatives, fatty acid esters of sorbitan and sulfated fatty alcohols which may be used alone or in combination.

Specific examples of excipients include sucrose, lactose, starches, crystalline cellulose, mannitol, light anhydrous silicic acid, magnesium aluminate, magnesium metasilicate aluminate, synthetic aluminium silicate, calcium carbonate, sodium hydrogen carbonate, calcium hydrogen phosphate and calcium carboxymethyl cellulose which may be used alone or in combination.

Lubricants usable in the present invention include magnesium stearate, talc and hardened oils as well as mixture thereof. Moreover, the antiviral agent of the present invention may further comprise corrigents such as those for improving taste and odor thereof, for example, common salt, sweetening agent, e.g., saccharin, sugar, mannitol, orange oil, glycyrrhiza extracts, citric acid, dextrose, menthol, eucalyptus oil and malic acid; perfumes, coloring agents and preservatives.

As auxiliary agents such as suspending agents and humectants, there may be mentioned, for example, coconut oil, olive oil, sesame oil, peanut oil, calcium lactate, safflower oil and soybean phospholipid.

Specific examples of the film-forming substances are derivatives of carbohydrates such as cellulose and sugars, for example, cellulose acetates phthalate (CAP); derivatives of polyvinyl compounds such as acrylic acid type copolymers and dibasic acid monoesters, for example, methyl acrylate-methacrylic acid copolymer and methyl methacrylate-methacrylic acid copolymer.

It is also possible, in coating the pharmaceutical compositions with the foregoing film-forming substances, to add, to the film-forming substance, a coating aid such as a plasticizer and various additives for preventing mutual adhesion between the pharmaceutical substances during coating operation for the purposes of improving the properties of the film-forming substances and making the coating operations much easier.

The reverse transcriptase inhibitor, the antiviral agent and the antiviral composition according to the present invention, which comprise at least on member selected from the group consisting of sulfated tyrosines and physiologically acceptable salts thereof as an effective component, have less toxicity and exhibit a remarkable inhibitory effect against a reverse transcriptase existing in viruses as well as a remarkable anti-AIDS viral activity.

The present invention will hereinafter be explained in more detail with reference to the following Synthesis Examples, Test Examples and Preparation Examples.

SYNTHESIS EXAMPLE 1

Synthesis of Sodium L-Tyrosine Sulfate 2 g of L-tyrosine, 5 g of trimethylamine complex of sulfur trioxide and 20 ml of pyridine were reacted for 93 hours at 55° C. under the atmosphere of nitrogen. After the reaction completed, the reaction mixture became two layers and the upper pyridine layer was removed, and then the remainder was washed with methylene chloride to remove pyridine. The resulting solution was poured into 200 ml of aqueous solution containing 12 g of sodium bicarbonate which was cooled and then insoluble matter was removed by filtration. 100 ml of aqueous solution containing 6.8 g of tetrabutylammonium hydrogen sulfate and 1.8 g of sodium bicarbonate was added to the filtrate and the mixture was then subjected to an extraction with methylene chloride. The resulting methylene chloride phase was dried over magnesium sulfate and then evaporated to dryness.

To the residue thus obtained, 200 ml of Amberlite IR 120 B(Na +) and 200 ml of water were added, and the mixture was stirred for one night at room temperature. The mixture was then filtered to remove Amberlite, and the resulting aqueous solution was washed with methylene chloride and then lyophilized. In result, 2.3 g of sodium L-tyrosine sulfate was obtained as white to pale yellowish-white powder.

The sodium L-tyrosine sulfate thus obtained gave the following IR and UV spectra.

IR absorption spectrum (see FIG. 1): $\nu_{max}$, cm$^{-1}$ (KBr): 3475, 1660, 1510, 1250, 1060, 1020, 880

UV absorption spectrum: $\lambda_{max}$, nm (H$_2$O): 263 ($\epsilon$=2.6× 10$^2$) $\lambda_{max}$, nm (0.1N hydrochloric acid): 263 ($\epsilon$=5.0×10$^2$)

From the above UV spectra, it can be seen that the above sample lacks the UV absorption at approximately 280 nm which is attributable to a phenolic hydroxyl group.

Other physicochemical properties of the sodium L-tyrosine sulfate are as follows:

(i) Appearance: powder of white to pale yellowish-white.

(ii) Melting point: above 300° C.

(iii) Elemental Analysis: C 37.7%, H 3.4%, N 4.8%, S 11.8%, ash 30.3%

7

(iv) Solvent solubility:
soluble in water, methanol and dimethyl sulfoxide
insoluble in acetone, ethylacetate, hexane and chloroform (v) Color reaction:
ninhydrin reaction; negative
ferric chloride reaction; negative The sodium L-tyrosine sulfate was analyzed by a high performance liquid chromatography (HPLC) under the following condition, and then a single peak was exhibited.

Separation column: YMC-Pack ODS-A (available from YMC Co.,Ltd.) 250×4.6 mm particle size: 5 µm pore size: 120 Å

Moving phase: acetonitrile:0.002M aqueous ammonium phosphate solution (pH 7.45)=2:8

Flow rate: 1.0 ml/min

Temperature in column: a room temperature

Wavelength for detection: 220 nm, 260 nm (UV detector)

Retention time: about 2 minutes (about 3 minutes for tyrosine under the same condition)

Figure 2:
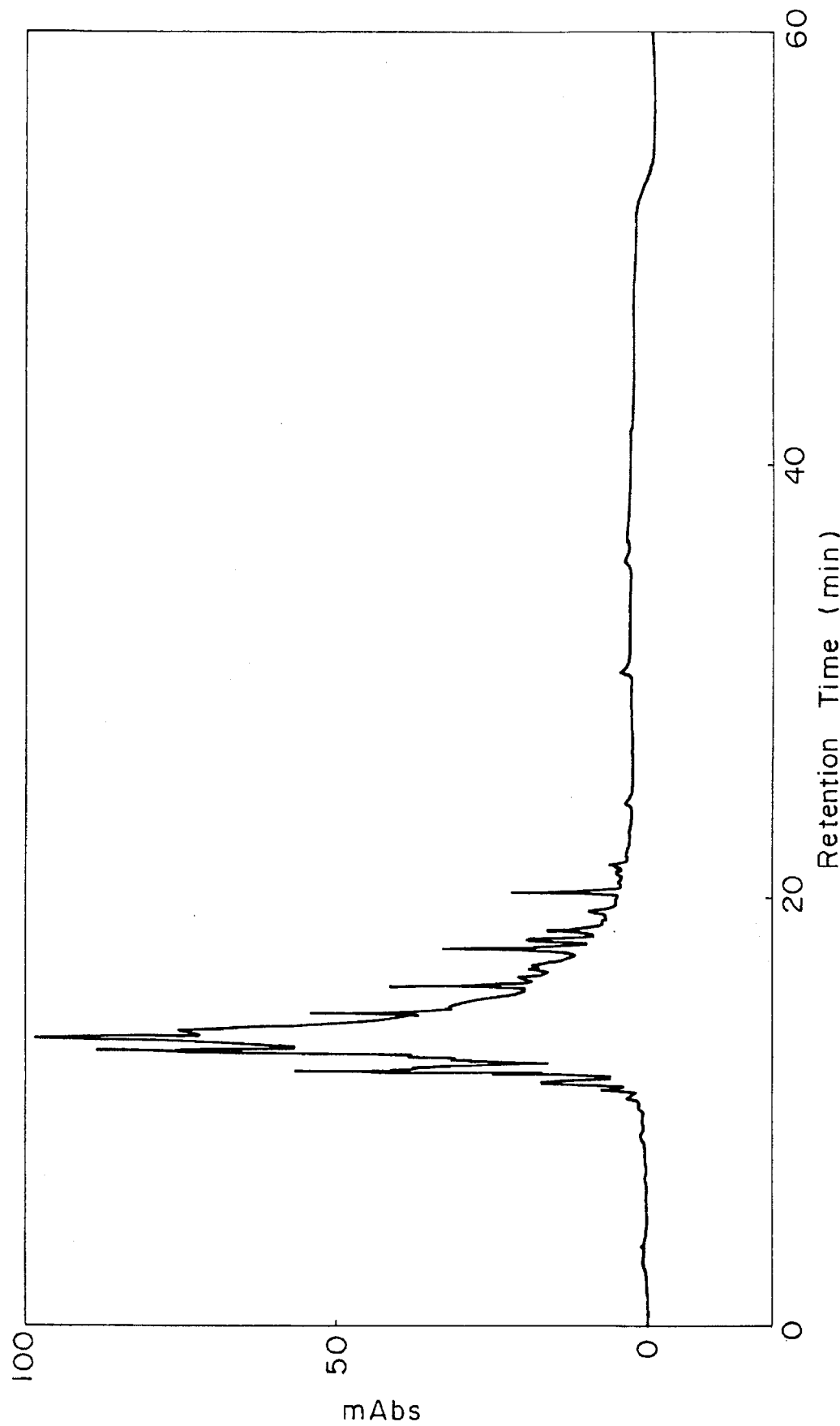
FIG. 2 is a chart of High Performance Liquid Charomatography (HPLC) chromatogram of sodium L-tyrosine sulfate synthesized in Synthesis Example 1.

The sodium L-tyrosine sulfate was also analyzed by HPLC under the following condition. As a result, about eight peaks were observed as exhibited in FIG. 2 and the main peak was found to have a retention time of 13.4 min.

Separation column: YMC-Pack ODS-A (available from YMC Co.,Ltd.) 250×4.6 mm particle size: 5 µm pore size: 120 Å

Moving phase:
A solution; 0.002M aqueous ammonium phosphate solution (pH 7.45)
B solution; acetonitrile:0.002M aqueous ammonium phosphate solution (pH 7.45)=2:8
linear gradient: A→B(100%) 30 min.

Flow rate: 1.0 ml/min

Temperature in column: 40° C.

Wavelength for detection: 220 nm (UV detector)

Further, 1 g of the sodium L-tyrosine sulfate was subjected to a chromatography using Sephadex LH-20 column (manufactured by PHARMACIA, LH-20:150 ml, ID 2.5 cm×42 cm) and methanol as an eluting solution. The eluate obtained was fractioned into each 10 ml.

Figure 3:
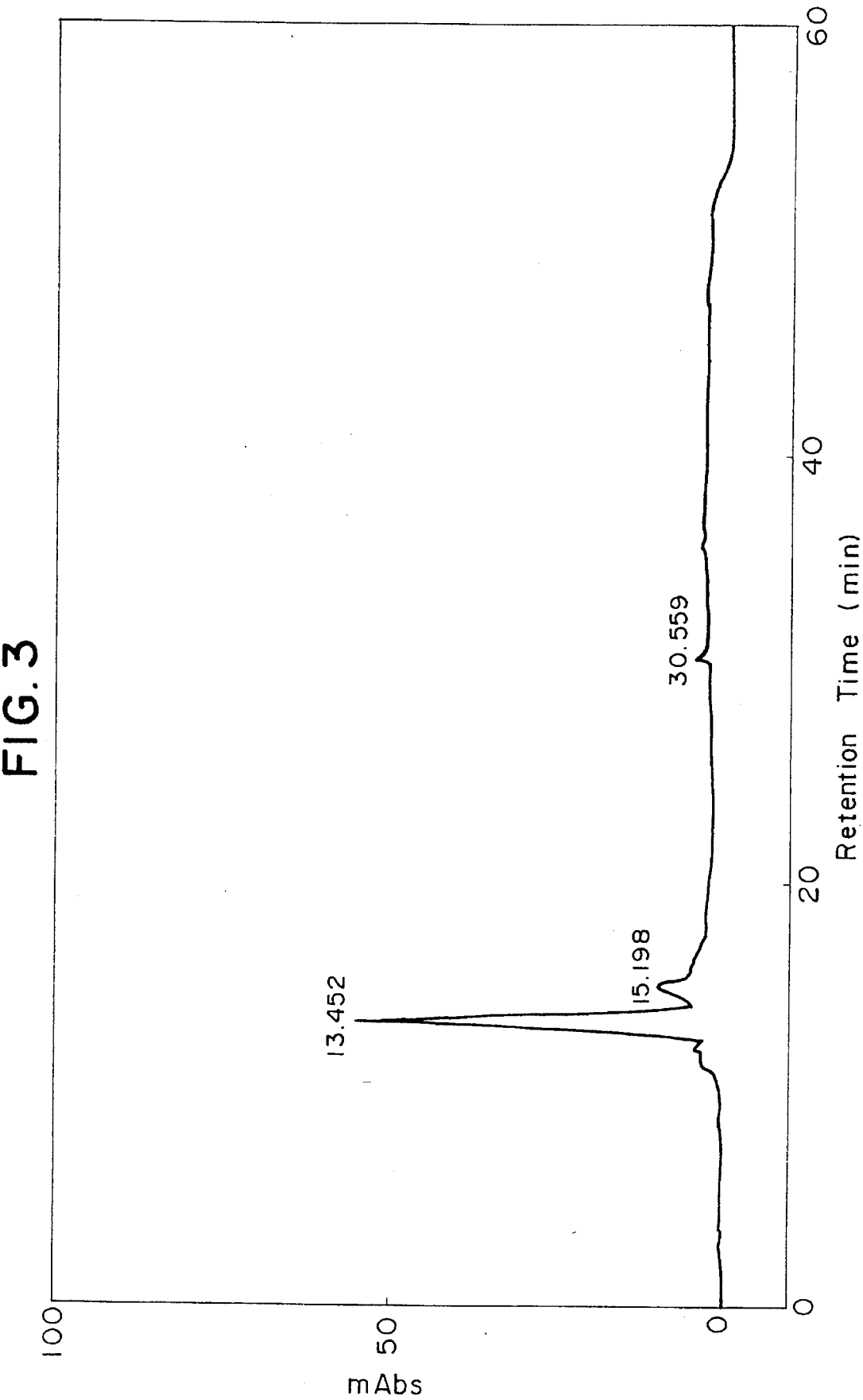
FIG. 3 is a chart of HPLC chromatogram of sodium L-tyrosine sulfate synthesized in Synthesis Example 1 and purified by Sephadex LH-20.

Fractions thus obtained were analyzed at an interval of several fractions by HPLC under the above condition. As a result, in fractions on and after the 88 th fraction, a single peak was observed as shown in FIG. 3 and the retention time thereof was about 13.4 min. This peak was found to be identical with the main peak shown in FIG. 2 which depicts a chromatogram of sodium L-tyrosine sulfate before purification by Sephadex LH-20.

The sodium L-tyrosine sulfate thus purified exhibited the following physicochemical properties.

Figure 4:
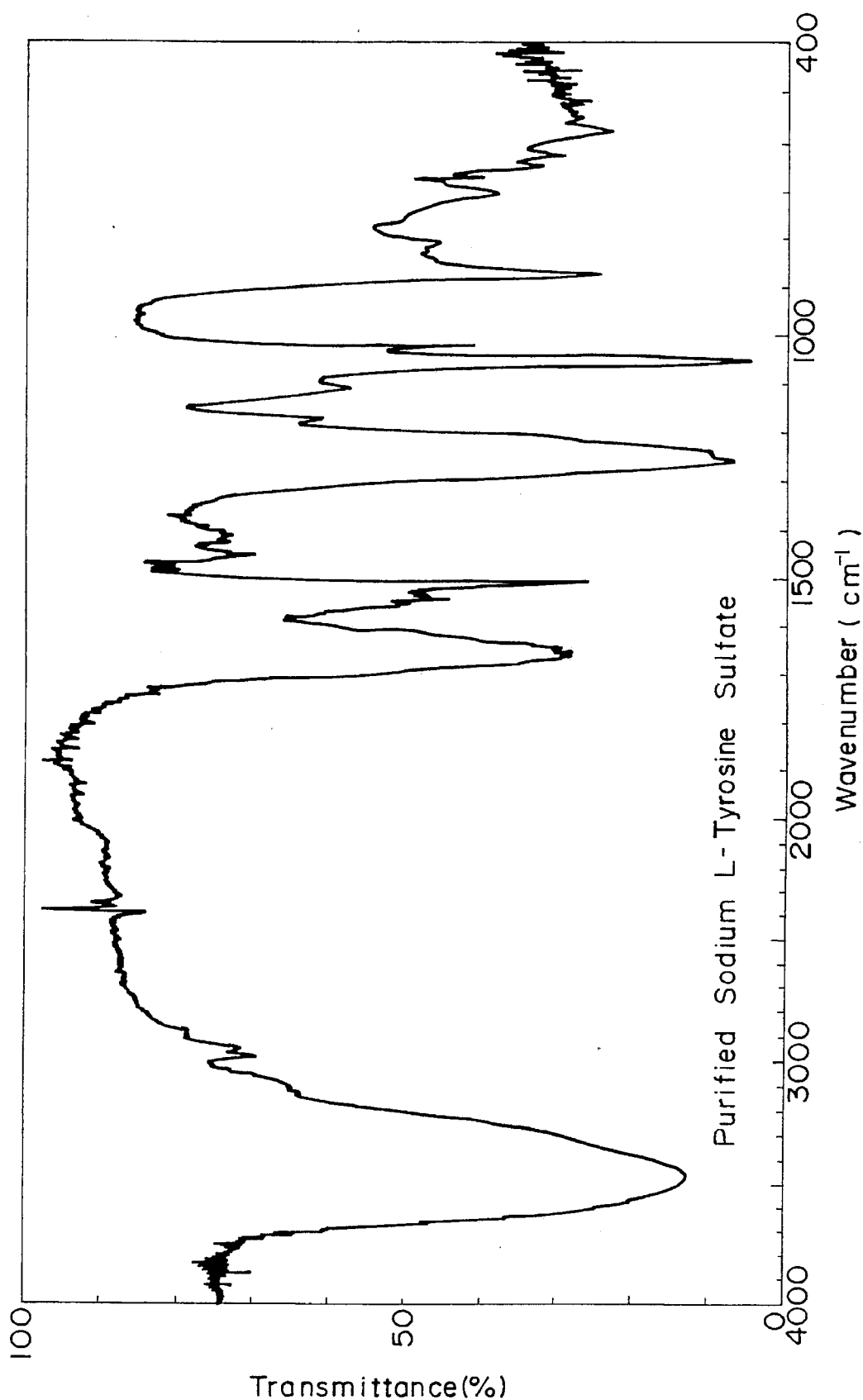
FIG. 4 is a chart of IR absorption spectrum of sodium L-tyrosine sulfate synthesized in Synthesis Example 1 and purified by Sephadex LH-20.

(i) IR absorption spectrum (see FIG. 4)

(ii) Appearance: powder of white to pale yellowish-white.

(iii) Melting point: above 300° C.

(iv) Solvent solubility:
soluble in water, methanol and dimethyl sulfoxide
insoluble in acetone, ethylacetate, hexane and chloroform (v) Color reaction:
ninhydrin reaction; negative
ferric chloride reaction; negative When the sodium L-tyrosine sulfate before the purification was heated in 0.1N hydrogen chloride solution for 10 minutes at 80° C. or in 6N hydrogen chloride solution for 20 hours at 105° C., the resulting hydrolyzed product exhibited $\lambda_{max}$ of UV absorption at 276 nm, which is specific to a phenolic hydroxyl group, and the absorption peak was shown to be identical with that of L-tyrosine.

When the above hydrolyzed product was also analyzed by HPLC and an amino acid-analyzer, a single peak was exhibited and the retention time thereof was same as that of L-tyrosine.

Accordingly, the sodium L-tyrosine sulfate herein synthesized is supposed to be a sodium salt of sulfated tyrosine wherein the phenolic hydroxyl group and/or the amino group is sulfated, and represented by the following formula:

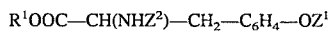

$$R^1OOC-CH(NHZ^2)-CH_2-C_6H_4-OZ^1$$

wherein either one of $Z^1$ and $Z^2$ is $-SO_3H$ or $-SO_3Na$, and the other is $-SO_3H$, $-SO_3Na$ or hydrogen atom; $R^1$ is hydrogen atom or sodium atom; and at least one of $Z^1$, $Z^2$ and $R^1$ includes sodium atom.

SYNTHESIS EXAMPLE 2

Synthesis of Sodium L-Tyrosine Sulfate

A sulfonating agent was used in the amount of one equivalent with respect to L-tyrosine to prepare sodium L-tyrosine sulfate.

Sodium L-tyrosine sulfate was prepared by repeating the procedure of Synthesis Example 1, provided that 1 g of L-tyrosine, 0.77 g of trimethylammonium complex of sulfur trioxide and 10 ml of pyridine were employed and reaction conditions were varied in the following three manners:

1. reaction temperature: 55° C., reaction time: 93 hours
2. reaction temperature: 100° C., reaction time: 3 hours
3. reaction temperature: 100° C., reaction time: 1 hour From the IR spectrum of each resulting product, each product was found to be the same compound as the sulfated tyrosine obtained by the reaction in Synthesis Example 1 wherein a sulfonating agent was used in an amount of 3.3 equivalent with respect to L-tyrosine.

When a sulfonating agent is used in an amount of 3.3 equivalent with respect to L-tyrosine, sulfated tyrosine can be quantitatively obtained. While when a sulfonating agent is used in an amount of one equivalent, an yield of the product is reduced to from 5 to 12% of the yield obtained when a sulfonating agent is used in an amount of 3.3 equivalent.

SYNTHESIS EXAMPLE 3

Synthesis of Sodium D-Tyrosine Sulfate 2 g of D-tyrosine, 5 g of trimethylamine complex of sulfur trioxide and 20 ml of pyridine were reacted for 93 hours at 55° C. under the atmosphere of nitrogen. After the reaction completed, the mixture became two layars and the upper pyridine layar was removed, and then the remainder was washed with methylene chloride to remove pyridine. The resulting solution was poured into 200 ml of aqueous solution containing 12 g of sodium bicarbonate which was cooled and then insoluble matter was removed by filtration. 100 ml of aqueous solution containing 6.8 g of tetrabutylammonium hydrogen sulfate and 1.8 g of sodium bicarbonate was added to the filtrate and the mixture was then subjected to the extraction with methylene chloride. The resulting methylene chloride phase was dried over sodium sulfate and then evaporated to dryness.

To the residue thus obtained, 200 ml of Amberlite IR 120 B(Na +) and 200 ml of water were added, and the mixture was stirred for a night at room temperature. The mixture was then filtered to remove Amberlite, and the resulting aqueous solution was washed with methylene chloride and then lyophilized. In result, 2.3 g of sodium D-tyrosine sulfate was obtained as white to pale yellowish-white powder.

Figure 5:
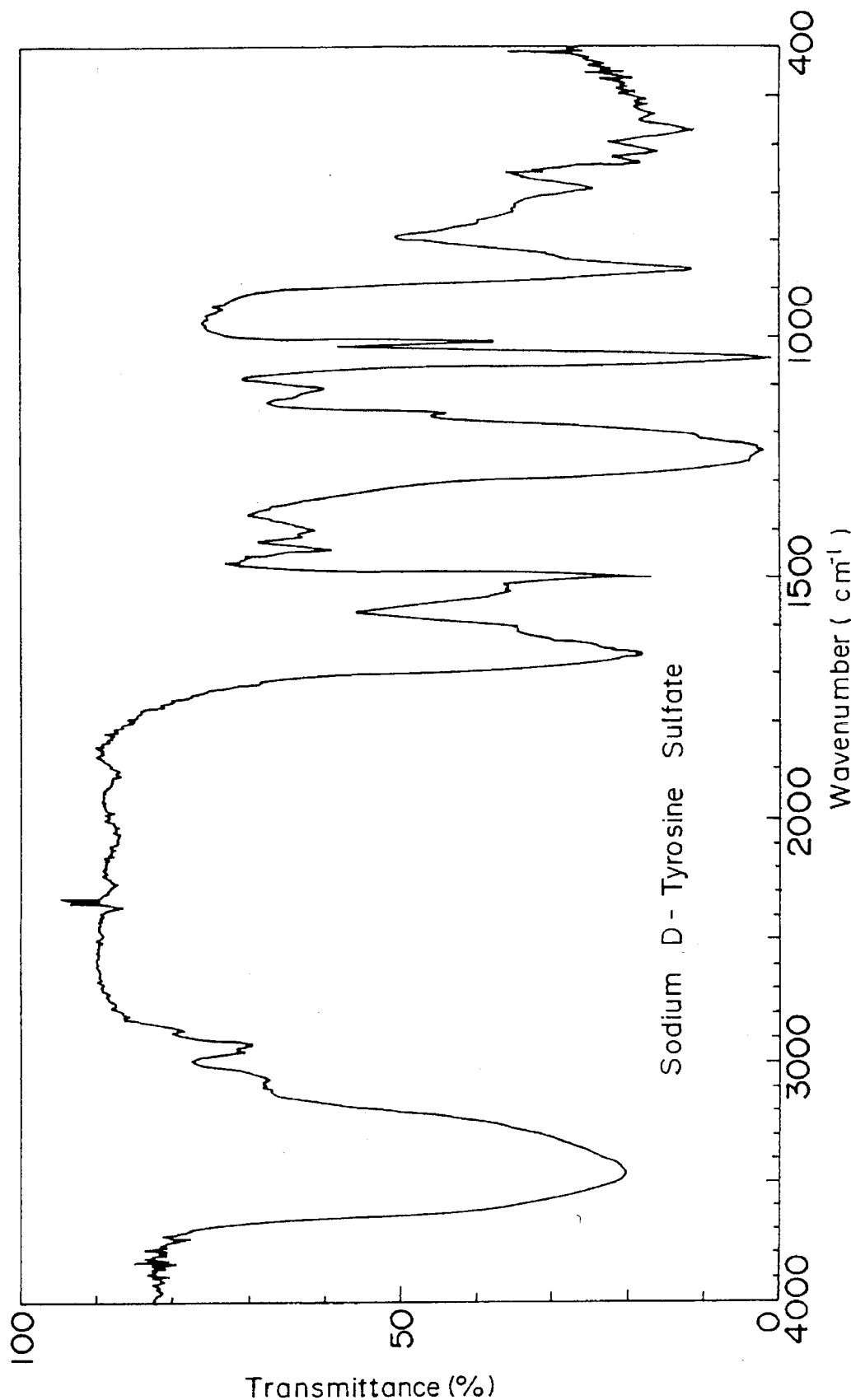
FIG. 5 is a chart of IR absorption spectrum of sodium D-tyrosine sulfate synthesized in Synthesis Example 3.

The sodium D-tyrosine sulfate thus obtained was confirmed by IR spectra and the result thereof is as follows:

IR absorption spectrum (see FIG. 5): $v_{max}$, cm$^{-1}$ (KBr): 3450, 1650, 1500, 1240, 1050, 1010, 860

SYNTHESIS EXAMPLE 4

Synthesis of Sodium L-Tyrosine Sulfate 2 g of L-tyrosine was added to 20 ml of pyridine and then the mixture was cooled in ice bath. 3.2 g of chlorosulfonic acid was added dropwise to the mixture. This reaction solution was subjected to a reaction at 55° C. for 93 hours under the atmosphere of nitrogen. After the reaction completed, the upper pyridine phase was removed and then the remainder was washed with methylene chloride to remove pyridine. The resulting solution was poured into 200 ml of aqueous solution containing 12 g of sodium bicarbonate which was cooled and then insoluble matter was removed by filtration. To this filtrate, 100 ml of aqueous solution containing 6.8 g of tetrabutylammonium hydrogen sulfate and 1.8 g of sodium bicarbonate was added and the resulting mixture was subjected to the extraction with methylene chloride. The resulting methylene chloride phase was dried over sodium sulfate and then evaporated to dryness.

To the residue thus obtained, 200 ml of Amberlite IR 120 B(Na +) and 200 ml of water were added, and the mixture was stirred for a night at room temperature. The mixture was then filtered to remove Amberlite, and the resulting aqueous solution was washed with methylene chloride and then lyophilized. In result, 2.6 g of sodium L-tyrosine sulfate was obtained.

SYNTHESIS EXAMPLE 5

Synthesis of Sodium L-Tyrosine Sulfate 2 g of L-tyrosine, 5 g of trimethylamine complex of sulfur trioxide and 20 ml of pyridine were reacted for one hour at 100° C. under the atmosphere of nitrogen. After the reaction completed, the reaction mixture became two layars and the upper pyridine layer was removed, and then the remainder was washed with methylene chloride to remove pyridine. The resulting solution was poured into 200 ml of aqueous solution containing 12 g of sodium bicarbonate which was cooled and then insoluble matter was removed by filtration. 100 ml of aqueous solution containing 6.8 g of tetrabutylammonium hydrogen sulfate and 1.8 g of sodium bicarbonate was added to the filtrate and the mixture was then subjected to the extraction with methylene chloride. The resulting methylene chloride phase was dried over sodium sulfate and then evaporated to dryness.

To the residue thus obtained, 200 ml of Amberlite IR 120 B(Na +) and 200 ml of water were added, and the mixture was stirred for a night at room temperature. The mixture was then filtered to remove Amberlite, and the resulting aqueous solution was washed with methylene chloride and then lyophilized. In result, 1.4 g of sodium L-tyrosine sulfate was obtained. The sodium L-tyrosine sulfate was confirmed by IR spectrum and the result thereof was as follows:

IR absorption spectrum: $v_{max}$, cm$^{-1}$ (KBr): 3475, 1660, 1510, 1250, 1050, 1020, 870

In the following Test Examples and Tests on Toxicity, there was used the sodium L-tyrosine sulfate synthesized in the above Synthesis Example 1.

Test Example 1

Inhibitory Effects of Sodium L-Tyrosine Sulfate on HIV-induced cell damage

In this test, there were used human T cell strain MT-4 cells (Gann monogr., Vol. 28, pp219–228 (1982)), which was tranformed with HTLV-1 which is an etiogenic virus of adult T cell leukemia, and HTLV-IIIB which is one of HIV strains. This test was performed in accordance with the method of Pauwels et al. (Pauwels et al., J. Virol. Methods, Vol. 20, pp309–21 (1988)).

Immediately after MT-4 cells were infected with HTLV-IIIB [MOI (multiplicity of infection =the number of inoculated virus/the number of cells): 0.01], sodium L-tyrosine sulfate and the HTLV-IIB-infected MT-4 cells were added to a microtiter plate having 96 wells at a variety of concentrations of sodium L-tyrosine sulfate and the concentration of $2.5 \times 10^4$ cells/well, respectively. These samples were cultivated at 37° C. for five days with carbon dioxide incubator. According to MTT method, the number of survival cells was then determined by measuring an absorbance to calculate an efficiency.

The result obtained was shown in the following Table 1.

TABLE 1

| Concentration (μg/ml) | Efficiency (%) |
| --- | --- |
| 1000 | 106 |
| 200 | 124 |
| 40 | 91 |
| 8 | 116 |
| 1.6 | 61 |
| 0.32 | −5 |
| 0 | 0 |

As seen from this Table, sodium L-tyrosine sulfate exhibited a remarkable anti-AIDS viral activity. Effective dose 50 ($ED_{50}$) thereof was found to be 1.22 g/ml.

Test Example 2

Determination of Reverse Transcriptase Inhibitory Effect

Reverse transcriptase inhibitory activity of sodium L-tyrosine sulfate was determined as follows:

20 μl of reaction solution was prepared so as to comprise 50 mM of Tris-hydrochloric acid buffer solution (pH 8.5), 40 mM of KCl, 6 mM of $MgCl_2$, 1 mM of dithiothreitol, 50 μg/ml of poly(A). oligo (dT)$_{12-18}$, [$\alpha^{-32}P$] deoxythymidine triphosphate, reverse transcriptase and sodium L-tyrosine sulfate.

After the reaction solution was incubated at 37° C. for 10 minutes, the reaction solution was deposited on DE 81 filter (available from Whatman). The filter was then washed thoroughly with 5% aqueous solution of $Na_2HPO_4$ and subsequently with water, ethanol and diethyl ether. Radiation of the filter was examined by scintillation counter and then the concentration which inhibits 50% of reverse transcriptase activity ($IC_{50}$) was calculated.

The reverse transcriptases used in this test were those derived from AMV (avian myeloblastosis virus) and HIV. $IC_{50}$'s were found to be 230 μg/ml against the reverse transcriptase derived from AMV and 36 μg/ml against the reverse transcriptase derived from HIV.

Tests on Toxicity (A) Influence on the Proliferation of T cells

As in Test Example 1, there was determined the influence of sodium L-tyrosine sulfate on the proliferation of HTLV-IIIB-non-infected MT-4 cells and the survival rate of the cells was calculated. The result obtained was shown in the following Table 2.

TABLE 2

| Concentration (μg/ml) | Survival rate (%) |
|---|---|
| 1000 | 112 |
| 200 | 120 |
| 40 | 94 |
| 8 | 110 |
| 1.6 | 97 |
| 0.32 | 98 |
| 0 | 100 |

(B) Influence on the proliferation of mice leukemia cell L1210

To the culture of mice leukemia cell L1210, sodium L-tyrosine sulfate was added at the concentration of 250 μg/ml and then the mixture was cultured for four days. As a result, sodium L-tyrosine sulfate exhibited hardly any inhibitory effects on the proliferation as compared with a control which was free of the compound.

(C) Acute toxicity on mice

Sodium L-tyrosine sulfate was intraperitoneally injected to male mice of ICR at age of 4 weeks at the dose of 500 mg/kg to examine an acute toxicity. As a result, there was not observed any remarkable toxicity.

Preparation Example 1

(Manufacture of Injections and Drugs for Drip)

Sodium L-tyrosine sulfate as an effective component was mixed with 5 g of powdered dextrose, followed by dispensing the mixture into vials so that 500 mg of the effective component was contained in each vial while maintaining an aseptic condition, sealing the vials, enclosing an inert gas such as nitrogen or helium gas in each vials and storing these vials at a low temperature in the dark. The drug thus prepared are dispersed in 500 ml of 0.85% physiological saline before use as an intravenous injection. The injection is intravenously injected or administered through drip in an amount ranging from 10 to 500 ml per day depending on the conditions of a patient.

Preparation Example 2

(Manufacture of Injections and Drugs for Drip)

An intravenous injection for a mild case was prepared in the same manner as used in Preparation Example 1 except that sodium L-tyrosine sulfate was used in an amount of 50 mg. The injection is intravenously injected or administered through drip in an amount ranging from 10 to 500 ml per day depending on the conditions of a patient.

Preparation Example 3

(Manufacture of Injections and Capsules)

Sodium L-tyrosine sulfate (30 mg) as an effective component was dissolved in a mixture comprising 1 g of purified sesame oil and 100 mg of aluminum steatate gel, followed by dispensing the mixture in a proper container, sealing the container, enclosing an inert gas such as nitrogen or helium gas in the container and storing it at a low temperature in the dark. The pharmaceutical preparation for subcutaneous injection thus prepared is subcutaneously injected once in an amount ranging from 1 to 10 ml per day depending on the conditions of a patient.

Alternatively, 0.5 ml each of the foregoing pharmaceutical preparation is dispensed in capsules to obtain those for orally administered. The capsules are orally administered in an amount ranging from 1 to 10 capsules per day depending on the conditions of a patient.

Preparation Example 4

(Manufacture of Enteric Coated Tablets)

In this Example, there were prepared 1,000 enteric coated tablets for each adult (i) and infant (ii) comprising the following components and having the following compositions.

| Components | (i) (g) | (ii) (g) |
|---|---|---|
| (A) | | |
| Sodium L-tyrosine sulfate | 100 | 50 |
| Lactose | 99.4 | 49.7 |
| Hydroxypropyl cellulose | 0.6 | 0.3 |
| Magnesium stearate | 2.0 | 1.0 |
| (B) | | |
| Cellulose acetate phthalate | 6.0 | 4.0 |
| Hydroxypropyl methylcellolose phthalate | 6.0 | 4.0 |

The components of the formulation (A) were mixed sufficiently and the resultant mixture was directly compressed to obtain tablets or the mixture was sufficiently kneaded, formed into granules by passing through a screen of an extrusion granulator, sufficiently dried and then compressed to form tablets.

Then, the formed tablets were coated with the molten formulation (B) to form enteric coated tablets.

Preparation Example 5

(Manufacture of Enteric Coated Granules)

Enteric Coated Granules (1,000 g) were formed from the following components.

| Component | Amount (g) |
|---|---|
| (A) | |
| Sodium L-tyrosine sulfate | 100 |
| Lactose | 737 |
| Hydroxypropyl cellulose | 3 |
| (B) | |
| Cellulose acetate phthalate | 80 |
| Hydroxypropyl methylcellulose phthalate | 80 |

The components of the formulation (A) were sufficiently mixed, formed into granules in an ordinary manner, and the granules were sufficiently dried and sieved to obtain the granules suitable for a bottle package or a heat-sealing package. Then the granules were coated with the molten formulation (B) while the granules were maintained in floating and flowing state to form enteric coated granules.

Preparation Example 6

(Manufacture of Enteric Coated Capsules)

In this Example, there were prepared 1,000 enteric coated capsuled for each adult (i) and infant (ii) comprising the following components and having the following compositions.

| Components | (i) (g) | (ii) (g) |
| --- | --- | --- |
| (A) | | |
| Sodium L-tyrosine sulfate | 100 | 50 |
| Lactose | 24.6 | 74.4 |
| Hydroxypropyl cellulose | 0.4 | 0.4 |
| (B) | | |
| Cellulose acetate phthalate | 10 | 10 |
| Hydroxypropyl methylcellulose phthalate | 10 | 10 |

The same procedures as used in Preparation Example 5 were repeated to form enteric coated granules suitable for capsules and the granules were encapsulated in capsules to obtaine enteric coated capsules.

What is claimed is:

1. A method for inhibiting reverse transcriptase activity of a retrovirus comprising contacting the retrovirus with an effective amount of sulfated L-tyrosine or its physiologically acceptable salt to inhibit the reverse transcriptase activity.

2. The method of claim 1 wherein the salt is selected from the group consisting of metal salts, inorganic acid salts and organic acid salts.

3. The method of claim 1 wherein the salt is selected from the group consisting of sodium, potassium, lithium, calcium, magnesium, barium, tetrabuytlammonium, hydrochloride, sulfate and acetate.

4. The method of claim 1 wherein the amount of sulfated tyrosine or its salt is from 1 mg to 10 g per day.

* * * * *